(12) United States Patent
Figueroa et al.

(10) Patent No.: US 6,685,740 B2
(45) Date of Patent: Feb. 3, 2004

(54) DEVICE FOR INSERTING A FLEXIBLE INTRAOCULAR LENS

(75) Inventors: Dennis Alexander Figueroa, Mission Viejo, CA (US); Alok Nigam, Trabuco Cyn, CA (US); Thomas Michael Heyman, Chino Hills, CA (US); Henry W. Oviatt, Jr., Mission Viejo, CA (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 09/977,961

(22) Filed: Oct. 17, 2001

(65) Prior Publication Data
US 2002/0022881 A1 Feb. 21, 2002

Related U.S. Application Data

(60) Division of application No. 08/615,185, filed as application No. PCT/US95/09973 on Aug. 7, 1995, now Pat. No. 6,336,932, which is a continuation-in-part of application No. 08/286,557, filed on Aug. 5, 1994, now abandoned.

(51) Int. Cl.[7] .................................................. A61F 2/16
(52) U.S. Cl. ........................ 623/6.12; 606/107; 128/898
(58) Field of Search .......................... 606/107; 128/898; 623/6.11, 6.12

(56) References Cited

U.S. PATENT DOCUMENTS

| 1,876,703 | A | | 9/1932 | Lilly |
| 2,761,446 | A | | 1/1956 | Reed |
| 3,991,426 | A | | 11/1976 | Flom et al. |
| 4,053,953 | A | | 10/1977 | Flom et al. |
| 4,214,585 | A | | 7/1980 | Bailey, Jr. |
| 4,244,370 | A | | 1/1981 | Furlow et al. |
| 4,573,998 | A | | 3/1986 | Mazzocco |
| 4,600,004 | A | | 7/1986 | Lopez et al. |
| 4,681,102 | A | | 7/1987 | Bartell |
| 4,699,140 | A | | 10/1987 | Holmes et al. |
| 4,702,244 | A | | 10/1987 | Mazzocco |
| 4,715,373 | A | | 12/1987 | Mazzocco et al. |
| 4,747,404 | A | | 5/1988 | Jampel et al. |
| 4,763,650 | A | | 8/1988 | Hauser |
| 4,765,329 | A | | 8/1988 | Cumming et al. |
| 4,822,360 | A | | 4/1989 | Deacon |
| 4,834,094 | A | | 5/1989 | Patton et al. |
| 4,836,201 | A | * | 6/1989 | Patton et al. ................ 606/107 |
| 4,836,202 | A | | 6/1989 | Krasner |
| 4,880,000 | A | | 11/1989 | Holmes et al. |
| 4,919,130 | A | | 4/1990 | Stoy et al. |
| 4,934,363 | A | | 6/1990 | Smith et al. |
| 4,955,889 | A | | 9/1990 | VanGent |
| 4,957,505 | A | | 9/1990 | McDonald |
| 4,976,716 | A | | 12/1990 | Cumming |
| 5,007,913 | A | | 4/1991 | Dulebohn et al. |
| 5,098,439 | A | | 3/1992 | Hill et al. |
| 5,123,905 | A | | 6/1992 | Kelman |
| 5,190,552 | A | | 3/1993 | Kelman |
| 5,242,450 | A | | 9/1993 | McDonald |
| 5,275,604 | A | | 1/1994 | Rheinish et al. ............ 606/107 |
| 5,304,182 | A | * | 4/1994 | Rheinish et al. ............ 606/107 |
| 5,395,378 | A | | 3/1995 | McDonald |
| 5,468,246 | A | * | 11/1995 | Blake ........................ 606/107 |

(List continued on next page.)

Primary Examiner—Glenn K. Dawson
(74) Attorney, Agent, or Firm—Katherine McGuire

(57) ABSTRACT

This invention is a device for inserting a flexible intraocular lens (12) into an eye comprising a tubular member (16) and a plunger (18). The tubular member includes a staging area (45), a lumen, and an open distal end (95). The staging area supports unstressed state prior to engagement by the plunger. In the unstressed state, the optic (48) of the lens is suspended in a pocket to avoid any substantial contact with interior portions of the tubular member. The plunger includes a slot (132) in its distal tip fo receiving and gripping the lens. With this construction, the lens can be inserted into the eye in one continuous motion. Further, the plunger holds the lens when the lens is moved out of the tubular member.

12 Claims, 10 Drawing Sheets

U.S. PATENT DOCUMENTS

| | | |
|---|---|---|
| 5,494,484 A | 2/1996 | Feingold |
| 5,496,328 A | 3/1996 | Nakajima et al. |
| 5,499,987 A | 3/1996 | Feingold |
| 5,562,676 A | 10/1996 | Brady et al. ............. 606/107 |
| 5,578,042 A * | 11/1996 | Cumming .............. 606/107 |
| 5,766,181 A | 6/1998 | Chambers et al. ......... 606/107 |
| 5,873,879 A * | 2/1999 | Figueroa et al. .......... 606/607 |

\* cited by examiner

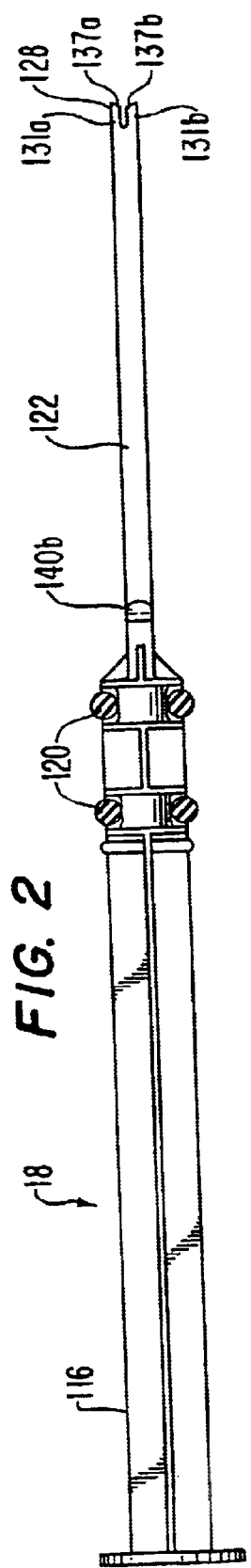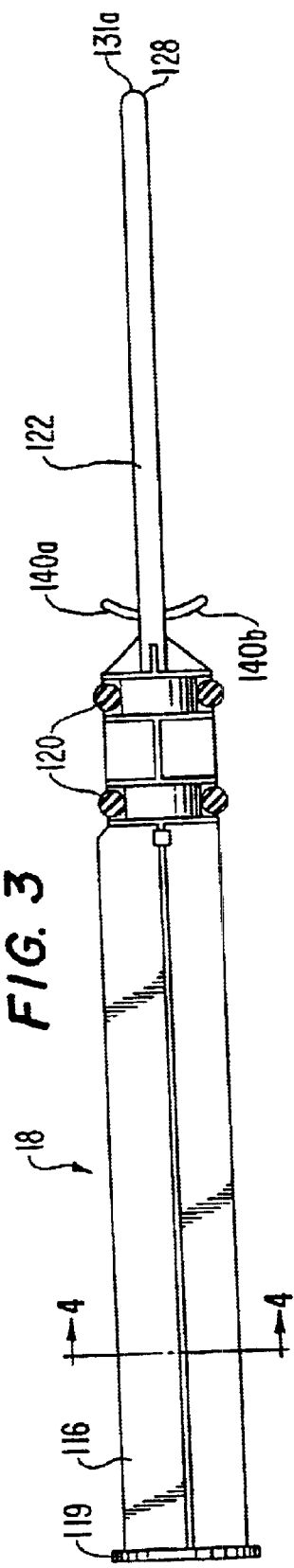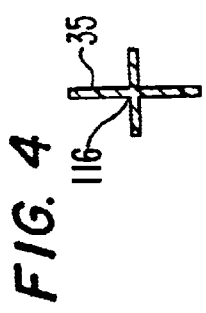

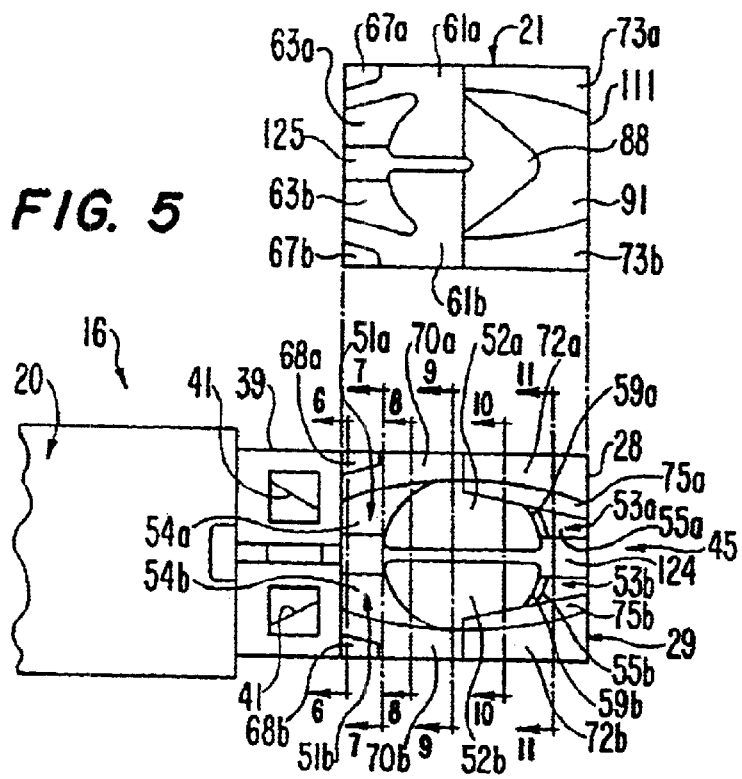
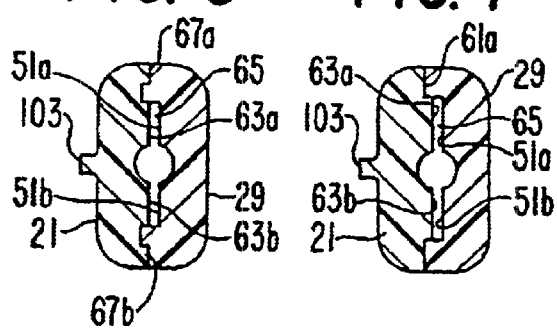
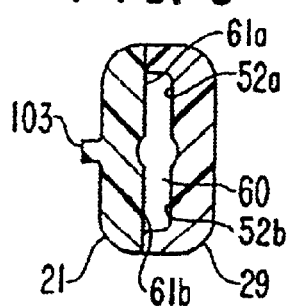
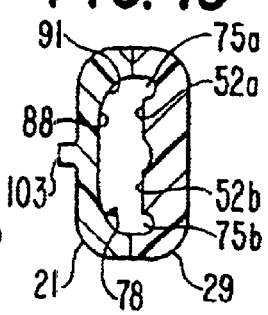
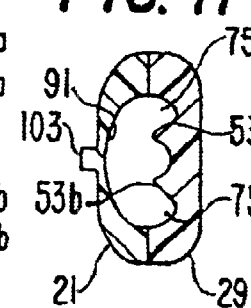
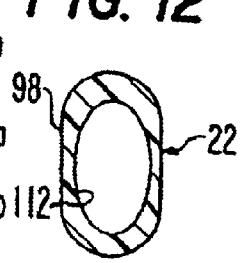

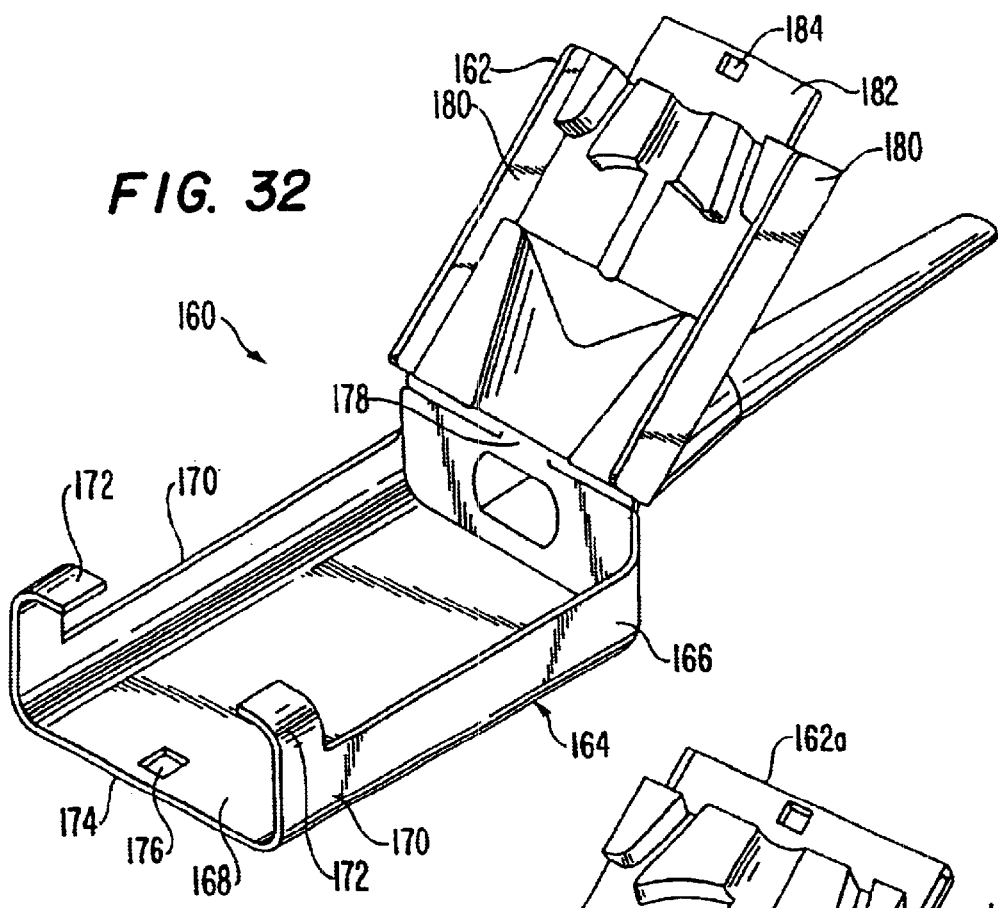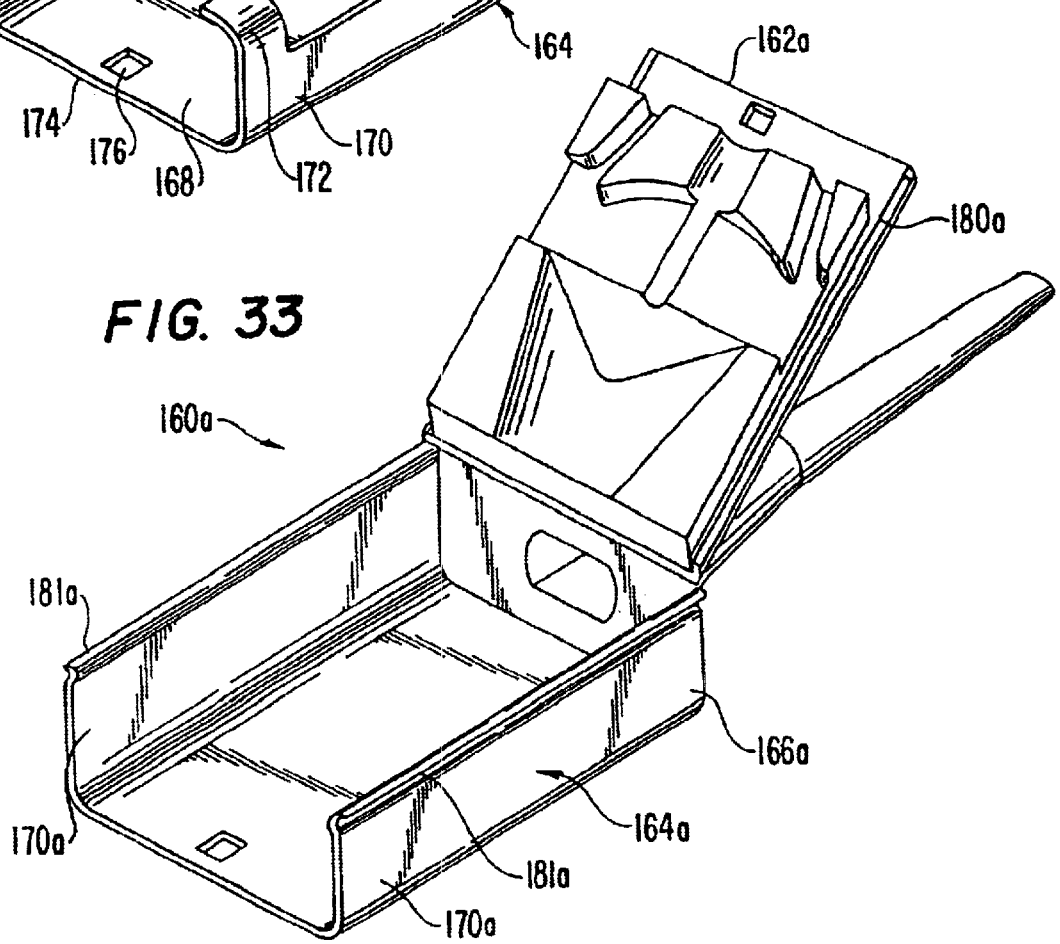

DEVICE FOR INSERTING A FLEXIBLE INTRAOCULAR LENS

This application is a division of application Ser. No. 08/615,185, filed Jun. 25, 1996, now U.S. Pat. No. 6,336,932, which is a 371 of PCT/US95/09973, filed Aug. 7, 1995, which is a continuation-in-part of application Ser. No. 08/286,557, filed Aug. 5, 1994, abandoned.

FIELD OF THE INVENTION

The present invention pertains to a device for inserting a flexible intraocular lens (IOL) into the eye of a patient.

BACKGROUND OF THE INVENTION

The natural crystalline lens of the eye plays a primary role in focusing light onto the retina for proper vision. However, the lens can become damaged due to injury or become cloudy because of the aging process or disease and form a cataract. To restore vision to the eye, the natural lens must be surgically removed and an artificial lens implanted as a replacement.

Many surgical procedures have been developed for removing the natural lens. As an example, phacoemulsification is one such process which has gained wide popularity. According to this procedure, a slender implement is inserted through an incision made in the eye and into the natural lens. The implement produces ultrasonic vibrations and emulsifies the lens. The emulsified portions of the lens are then aspirated out of the eye through a passage provided in the implement. As opposed to other procedures, this lens extraction method requires the surgeon to make only a narrow incision in the eye. In general, the use of a small incision can lessen the trauma and complications experienced during the surgery and postoperatively.

A flexible IOL comprises a central optic portion which focuses light on the retina and at least one outwardly extending haptic. Haptics can have a variety of different configurations, but most commonly are either a plate-like extension of the optic or loop shaped. In any event, the haptics extend outwardly to position the optic of the lens in alignment with the pupil. Flexible IOLs are particularly suited for insertion in the eye following a phacoemulsification lens extraction procedure. Whereas placement of a hard, non-foldable IOL would require widening of the small phacoemulsification incision, a flexible IOL can be compressed or folded for passage through the narrow incision in the eye. Once the lens is passed through the incision and released into the eye, it will expand to its original shape and size.

A number of different devices have been developed to implant a flexible IOL into an eye. See, for example, U.S. Pat. No. 4,573,998 to Mazzocco, U.S. Pat. No. 4,681,102 to Bartell, U.S. Pat. No. 4,919,130 to Stoy et al., and U.S. Pat. No. 5,275,604 to Rheinish et al. In general, these devices function to pass a compressed lens through the narrow incision made in the eye. These devices, however, require undue manipulation of the lens, include a multiplicity of parts, and/or fail to provide ample control of the lens as it enters the eye.

SUMMARY OF THE INVENTION

The present invention is a device which enables flexible IOLs to be easily folded, compressed and inserted through an incision in the eye. In general, the insertion device comprises a tubular member for receiving the lens and a plunger for pushing the lens through the tubular member and into the eye. As the lens is pushed through the passage it is compressed into a smaller configuration. The construction of the present invention ensures an easy, sure and consistent compression of the lens.

According to one aspect of the invention, the tubular member includes a staging area for holding the lens in an unstressed condition. The lens is preferably held in a suspended position by its haptics so that the optic remains substantially free of contact with the interior of the tubular member. In this manner, the device can be used as the lens package, and the device can be shipped and stored with the lens already in place and ready for use. As a result, unnecessary manipulation of the lens is avoided. According to another aspect of the invention, the plunger tip is provided with a structure which holds the lens to the plunger when the lens is pushed out of the tubular member. The distal tip of the plunger is preferably bifurcated to define a slot for partially receiving and gripping the lens. With this construction, the plunger is able to hold the lens when the lens exits the tubular member and expands into the eye. Holding the lens in this manner eases placement of the lens in the eye and alleviates the risks associated with uncontrolled unfolding of the lens or uncontrolled expulsion of the lens from the inserter into the eye.

BRIEF DESCRIPTION OF THE DRAWINGS

FIG. 2 is a side elevational view of the plunger of the insertion device.

FIG. 3 is a top plan view of the plunger.

FIG. 4 is a cross sectional view taken along line 4—4 in FIG. 3.

FIG. 5 is a partial top plan view of the tubular unit of the insertion device, including the staging area, with the cover removed and overturned, and the cannula omitted.

FIG. 6 is a cross sectional view taken along line 6—6 in FIG. 5 with the cover placed onto the shelf segment.

FIG. 7 is a cross sectional view taken along line 7—7 in FIG. 5 with the cover placed onto the shelf segment.

FIG. 8 is a cross sectional view taken along line 8—8 in FIG. 5 with the cover placed onto the shelf segment.

FIG. 9 is a cross sectional view taken along line 9—9 in FIG. 5 with the cover placed onto the shelf segment.

FIG. 10 is a cross sectional view taken along line 10—10 in FIG. 5 with the cover placed onto the shelf segment.

FIG. 11 is a cross sectional view taken along line 11—11 in FIG. 5 with the cover placed onto the shelf segment.

FIG. 12 is a cross sectional view along line 12—12 in FIG. 13.

FIG. 32 is a perspective view of an alternative embodiment of the cannula.

FIG. 33 is a perspective view of another alternative embodiment of the cannula.

DETAILED DESCRIPTION OF THE PREFERRED EMBODIMENTS

Figure 1:
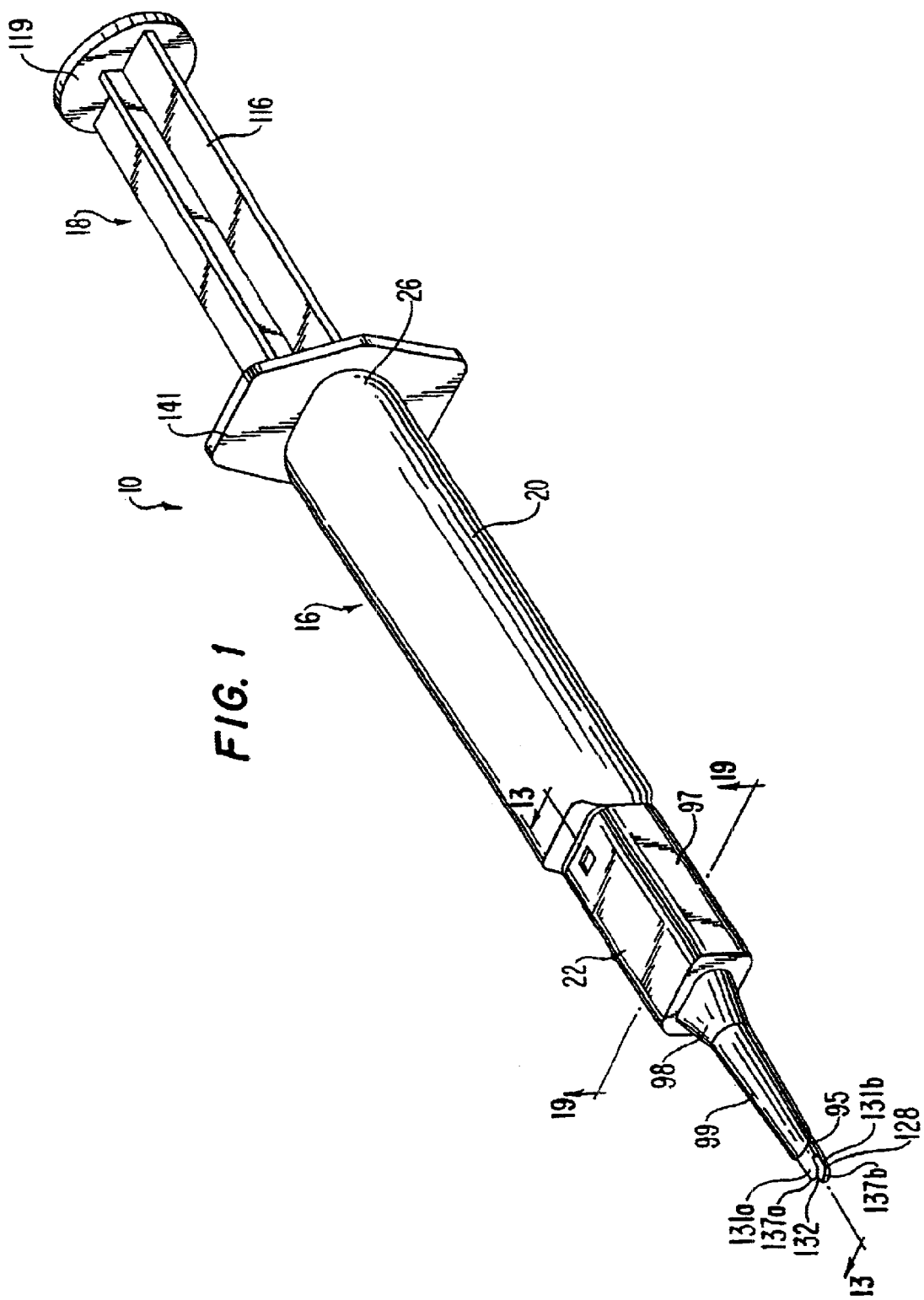
FIG. 1 is a perspective view of an insertion device in accordance with a preferred embodiment of the present invention.
Figure 13:
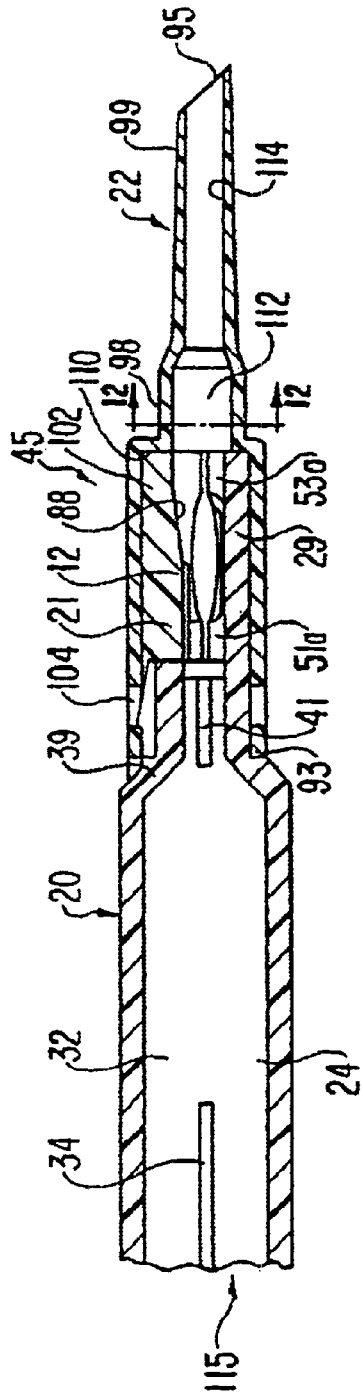
FIG. 13 is a partial cross sectional view taken along line 13—13 in FIG. 1, with an IOL in the staging area.
Figure 14:
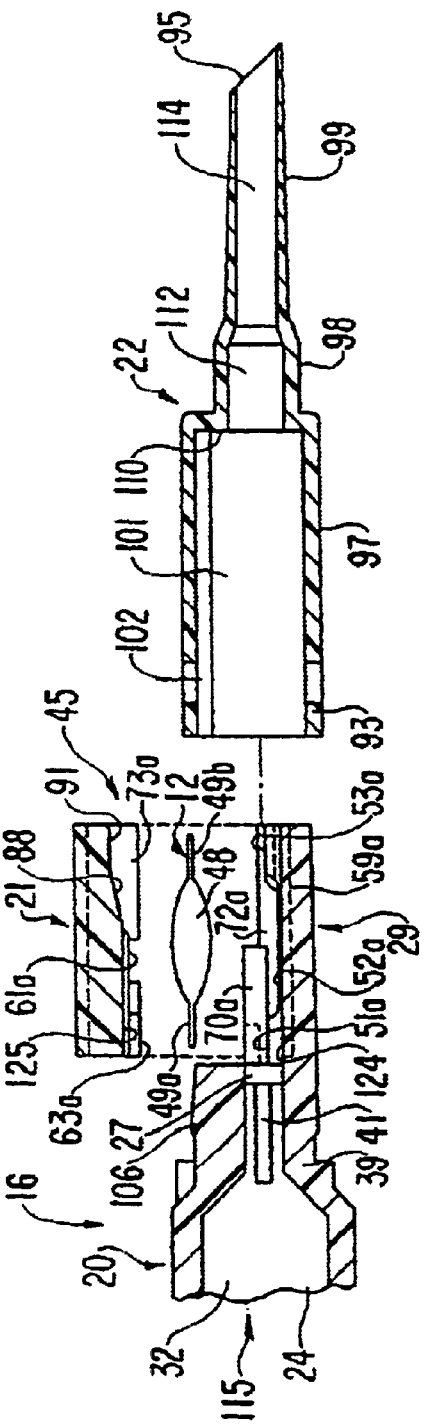
FIG. 14 is an exploded view of FIG. 13.
Figure 15:
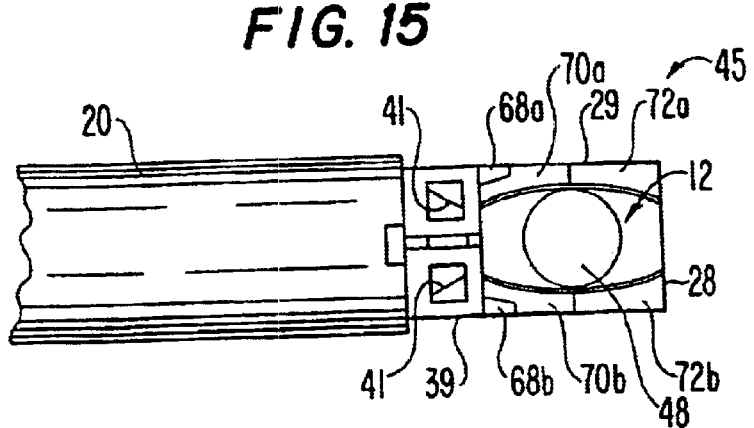
FIG. 15 is a partial top plan view of the tubular unit of the insertion device with an IOL in the staging area and with the cover and cannula omitted.
Figure 16:
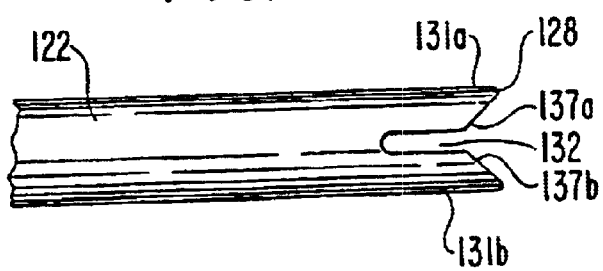
FIG. 16 is side elevational view of the distal tip of the plunger.
Figure 17:
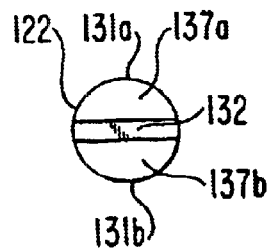
FIG. 17 is a front view of the distal end of the plunger.
Figure 18:
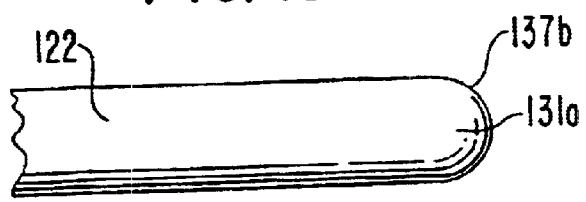
FIG. 18 is a top plan view of the distal end of the plunger.
Figure 26:
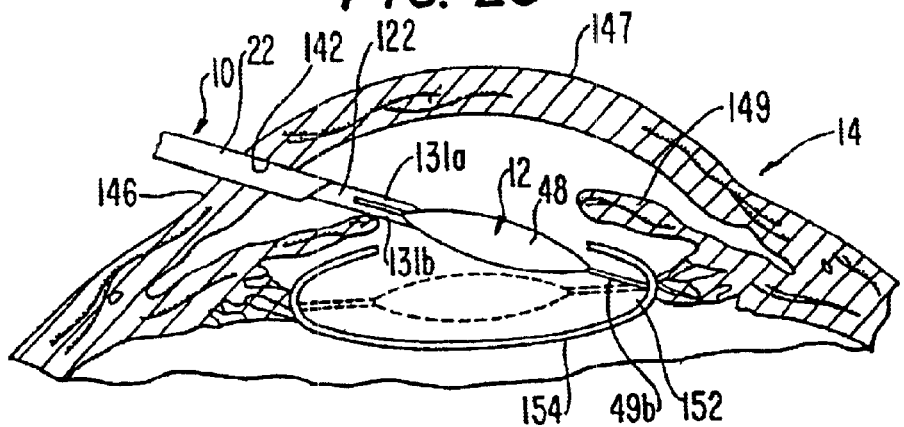
FIG. 26 is a cross sectional view of an eye illustrating the insertion and placement of an IOL.

The present invention pertains to a device 10 (FIG. 1) for inserting a flexible IOL 12 into an eye 14 of a patient (FIG. 26). The device comprises an outer tubular unit 16 and an inner plunger 18. In one embodiment, tubular unit 16 is formed by a base member 20, a cover 21 and a cannula 22 which are coupled together (FIGS. 1, 13 and 14). The components of device 10 may be composed of a plastic or metal material. For example, the components can be formed of polycarbonate or polypropylene. The plunger 18 and cannula 22 are preferably made of polypropylene. Nevertheless, a wide array of materials could be used.

Base member 20 is an elongate tubular member defining an inner passage 24 which is provided with a relatively large opening at proximal end 26 and an opening 27 of reduced size near, but spaced from, distal end 28 (FIGS. 1, 5, 13 and 14). A forwardly extending shelf segment 29 projects beyond opening 27 (FIGS. 5, 13 and 14). Base member 20 preferably has generally oval cross sectional configuration, although other shapes could be used.

The inner passage 24 of base member 20 is adapted to movably receive therein plunger 18. A longitudinal groove 34 is preferentially positioned along one of the side walls 32 defining inner passage 24 (FIG. 13). Groove 34 cooperates with an extending flange 35 projecting laterally from plunger 18 to ensure that the plunger is properly oriented when fed into base member 20. Nevertheless, the groove construction could be replaced with a different structure for ensuring proper placement, such as forming at least a portion of inner passage 24 and plunger 18 with a D-shaped configuration. Near distal end 28, base member 20 forms a narrowed neck 39. Neck 39 defines distal opening 27 through which a portion of the plunger is passed to engage lens 12. Converging guideways 41 are positioned along opposite interior sides of passage 24 leading up to neck 39 FIGS. 5, 13 and 14). Guideways 41 function to ease the passage of the plunger through neck 39 and over the shelf segment 29 for engagement with lens 12.

Figure 24:
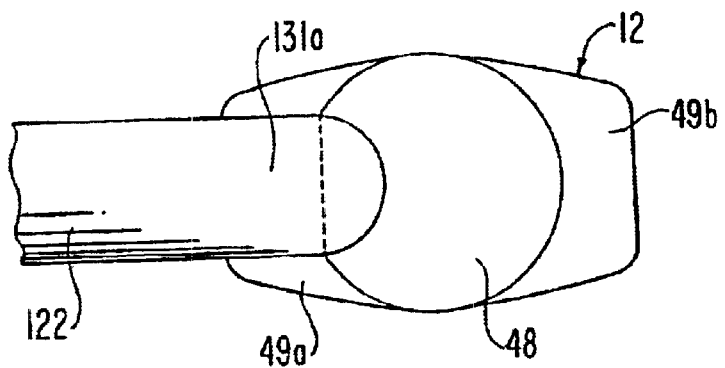
FIG. 24 is an enlarged top plan view of the distal tip of the plunger holding an IOL.

Shelf segment 29 is formed as an extension of roughly one half of the tubular base member 20. Shelf segment 29 cooperates with cover 21 to define a staging area compartment 45 for holding lens 12 (FIGS. 5–11 and 13–14). Lens 12 preferably has a central optic and a pair of adjacent web or plate haptics 49a, 49b (FIGS. 14 and 24). Nevertheless, other lens constructions, such as a lens with loop haptics, could also be used. The interior side of shelf segment 29 is formed in part by a pair of ledges 51a, 51b adjacent neck 39, a pair of recessed central flats 52a, 52b, and a pair of ramps 53a, 53b spaced forwardly of flats 52a, 52b (FIGS. 5–11 and 13–14). Ledges 51a, 51b and ramps 53a, 53b are each formed with top surfaces 54a, 54b, 55a, 55b to engage and support the haptics 49a, 49b of lens 12 in an initial unstressed position. Ramps 53a, 53b further include sloped surfaces 59a, 59b inclined to flats 52a, 52b. Flats 52a, 52b are recessed relative to top surfaces 54a, 54b, 55a, 55b to define a pocket 60 into which is received optic 48.

Cover 21 lies against shelf segment 29 to form staging area compartment 45 and enclose lens 12 in its initial unstressed position (FIG. 13). Cover 21 includes on its interior side recessed sections 61a, 61b, the central portions of which lie opposed to the proximal half of flats 52a, 52b. A pair of adjacent plateau segments 63a, 63b lie opposed to ledges 51a, 51b to define a gap 65 adapted to matingly receive and hold the proximal haptic 49a. Haptic 49a is loosely received in gap 65 so that it can be easily pushed out of staging area 45 during the insertion process. Ledges 51a, 51b, plateau segments 63a, 63b, and ramps 53a, 53b collectively support lens 12 by haptics 49a, 49b. In this initial position, optic 48 is held in suspension in pocket 60 so that the optic avoids contact with the interior walls of the staging area compartment 45.

The lens 12 can be installed in compartment 45 at a manufacturing plant and shipped to is the user in device 10 with or without cannula 22 assembled in place. In this manner, device 10 can conveniently serve also as a lens package. Since lens 12 is supported in a generally suspended and unstressed state, the lens can be stored for a substantial length of time, perhaps as long as 10 years. Although the cover could be fixed to base member 20, it is designed for removal to enable inspection of the lens prior to its implantation in the eye. As shown in FIG. 14, cover 21 can be separable from base member 20, and secured in place by a snap fit, tape or other securing means. Nevertheless, the cover may be hinged to cannula 22, shelf segment 29, or neck 39.

Cover 21 includes projections 67a, 67b which mate with depressions 68a, 68b formed in shelf segment 29. In addition, shelf segment 29 includes proximal outer walls 70a, 70b and distal outer walls 72a, 72b. Proximal walls 70a, 70b abut the outer portions of recessed sections 61a, 61b. Distal walls 72a, 72b likewise abut walls 73a, 73b of cover 21. Distal walls 72a, 72b are preferably recessed relative to proximal walls 70a, 70b to enhance the mating fit of cover 21. During shipping of the device, the cover may be held closed by cannula 22, tape and/or other means to avoid inadvertent release of the lens.

Troughs 75a, 75b are formed in shelf segment 29 by extending the inner side wall surface 78 of compartment 45 downwardly between the outer distal sides of flats 52a, 52b and distal walls 72*a*, 72*b*. Troughs 75*a*, 75*b* are provided to receive the opposite sides of lens 12 as they are folded or curled along inner side wall surface 78. In the preferred embodiment, the troughs are deeper than flats 52*a*, 52*b*.

Cover 21 further-includes a central, generally planar surface 88 inclined to extend away from shelf segment 29. A conically shaped portion 91 generally surrounding inclined surface 88 lies opposed to ramps 53*a*, 53*b*. These surfaces 88, 91 in cooperation with ramps 53*a*, 53*b* initiate the desired folding of the lens to its compressed state.

Cannula 22 is an elongate tubular member with an open proximal end 93 and an opposite open distal end 95 (FIGS. 1 and 12–14). Cannula 22 is preferably subdivided into three graduated sections 97–99. The proximal section 97 has a generally rectangular configuration and defines an inner cavity 101 sized to matingly receive the assembled shelf segment 29 and cover 21. Section 97 extends from distal end 28 to neck 39 of base member 20 and functions to hold cover 21 against shelf segment 29. An axial channel 102 is defined along one wall of cavity 101 to matingly receive ridge 103 extending up from cover 21. A hole 10 defined at the proximal end 93 of cannula 22 cooperates with a biased lock 106 on base member 20 to secure the cannula in place.

The medial section 98 of cannula 22 is significantly smaller than proximal section 97 so that a rim 110 is defined therebetween. Rim 110 acts as a shoulder in abutment with the aligned distal ends 28, 111 of base member 20 and cover 21. The inner wall of medial section 98 converges to define a funnel shaped passage 112. The funnel portion 112 preferably has an oval cross section, although other shapes could be used. This funnel section causes the lens to become substantially curled and compressed for entry into the eye.

The final, distal section 99 of cannula 22 is a long, narrow tube which defines an inner lumen 114. Distal section 99 is to be inserted through the narrow incision made in the eye. As with medial section 98, distal section 99 and lumen 114 preferably have an oval cross sectional shape. Of course, other shapes could be utilized if desired. To facilitate manufacturing and further compression of lens 12, lumen 114 is formed to taper slightly as it extends forward. Distal end 95 of cannula 22 is beveled to ease the insertion of the cannula into the incision and to assist in facilitating a gradual expansion of the lens as it exits from lumen 114.

Figure 27:
FIG. 27 is a perspective view of an alternative construction of the distal end of the cannula.
Figure 28:
FIG. 28 is a perspective view of a second alternative construction of the distal end of the cannula.
Figure 29:
FIG. 29 is a perspective view of a third alternative construction of the distal end of the cannula.
Figure 30:
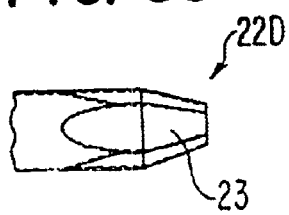
FIG. 30 is a side elevational view of a fourth alternative construction of the distal end of the cannula.
Figure 31:
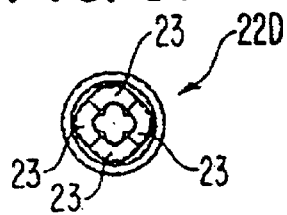
FIG. 31 is a front elevational view of the fourth alternative construction of the distal end of the cannula.
Figure 34:
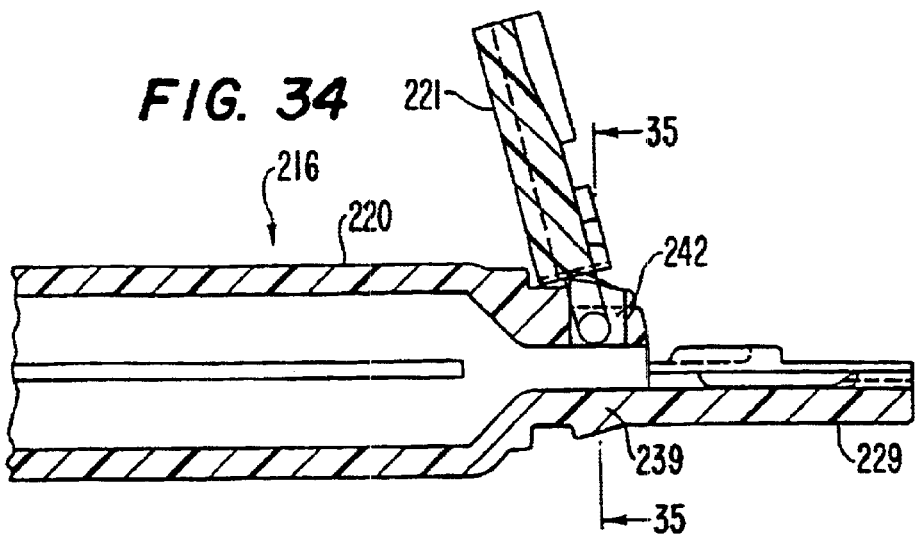
FIG. 34 is a partial, longitudinal cross sectional view of an alternative embodiment of the tubular unit with the cover open and the cannula removed.
Figure 35:
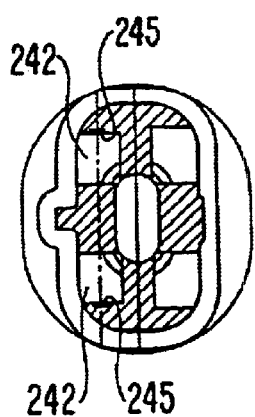
FIG. 35 is a cross sectional view taken along line 35—35 in FIG. 34, without the cover.
Figure 36:
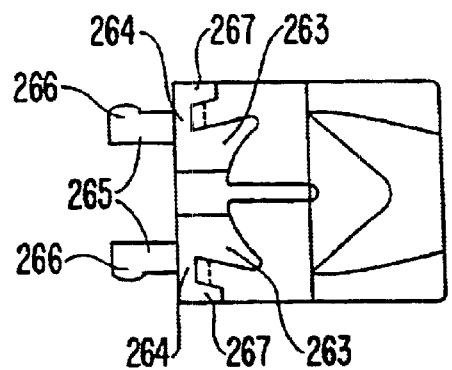
FIG. 36 is a plan view of the inside of the cover of the alternative tubular unit embodiment of FIG. 34.

The distal section of the cannula may be provided with a wide variety of cross section configurations. As examples only, the cannula may be shaped with a clover-type tip 22A, a collapsible bag type tip 22B, or a wave-type tip 22C (FIGS. 27–29). These configured tips enhance the strength of the tip and thus permit a narrower construction to be used. The cannula tip may also be formed with a collet-like construction 22D. In this embodiment, the tip includes four separable leaves 23 which are expanded as the lens is pushed into the eye. The leaves 23 are biased to naturally close after the lens is placed into the eye and the plunger retracted.

Figure 37:
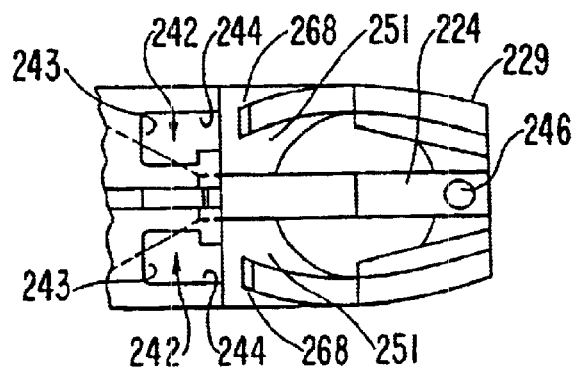
FIG. 37 is a plan view of the inside of the shelf segment of the alternative tubular unit embodiment of FIG. 34.

In the preferred embodiment, cover 221 is hinged to base member 220 of tubular unit 216 (FIGS. 34–37). The inside configuration of cover 221 is essentially the same as the inside configuration of cover 21, except that projections 267 are interconnected with plateau segments 263 by segments 264. Similarly, the inside configuration of shelf segment 229 is essentially the same as the inside configuration of shelf segment 29. As can be seen in FIG. 37, shelf segment 229 includes a corresponding interconnection of depressions 26 with ledges 251. Also, the central channel 224 of shelf segment 229, which accommodates passage of the plunger, is enlarged across its middle section. These modifications do not affect the operation of compressing and inserting the lens into an eye.

Also, as an optional feature, a hole 246 may be provided through shelf segment 229. The hole can be used to insert a viscoelastic material in embodiments wherein the cover is fixed to the shelf segment or otherwise not opened by the surgeon.

Cover 221 further includes a pair of rearwardly extending arms 265, which are provided with knobs 266 on their free ends. Arms 265 are provided to pivotally connect the cover to neck portion 239. Specifically, neck portion 239 includes a pair of sockets 242. Sockets 242 are formed to include substantially square shaped openings 243 (although other shapes could also be used) for receiving knobs 266, and channel portions 244 for receiving arms 265 when cover 221 is moved to its closed position (not shown). Recesses 245 are formed on the outside walls of openings 243 (FIG. 35) to receive the outward projection of knobs 266. Receipt of knobs 266 in recesses 245 functions to retain the cover 221 to base member 220.

In an alternative embodiment, cannula 160 includes a cover 162 hinged for movement between an open position and a closed position (FIG. 32). Cannula 160 has essentially the same construction as cannula 22, except for the incorporation of cover 162 in proximal section 164. Cover 162 has substantially the same construction as cover 21, including the same internal configuration for supporting and compressing the lens.

Proximal section 164 of cannula 160 comprises a base 166 and a cover 162. The base includes a bottom wall 168 and a pair of side walls 170 which extend upward only as high as shelf segment 29. The internal surfaces of bottom wall 168 and side walls 170 are shaped to matingly receive the external surface of shelf segment 29. A pair of upstanding flanges 172 are provided at proximal end 174 of base 166 to engage neck 39 and provide ample support for the cannula. A hole 176 is provided to cooperate with a protrusion (not shown) on shelf segment 29 in locking the cannula to the base member 20.

Cover 162 is movably connected to base 166 by a living hinge 178, although other hinge constructions could also be used. The cover is pivotally movable to an open position to permit inspection of the lens, and to a closed position for inserting the lens into a patient's eye. The lower edges of side walls 180 of the cover are formed to snap into a locking engagement with base 166 by any conventional construction (not shown); nevertheless, other fastening arrangements could be used. The internal configuration of cover 162 aligns with the internal configuration of shelf segment 29 in the same way as cover 21. Cover 162 further includes a proximal tab 182 which projects between flanges 172 to engage locking protrusion 106 in hole 184.

As an alternative construction, side walls 170*a* of cannula 160*a* extend the entire depth of proximal section 164*a*, and cover 162*a* is provided with a flattened construction (FIG. 33). The internal side of cover 162*a* has the same configuration and relative positioning to shelf segment 29 as does the above-described cover 21. The edges 180*a* of cover 162*a* are preferably constructed to snap into locking engagement with edges 181*a* of side walls 170*a*. Nonetheless, other fastening arrangements could be used.

Preferably, cannula 162, 162*a* is composed of a polypropylene or other thermoplastic material. A disposable cover (not shown), can be used to ship and store the IOL in device 10. The disposable cover preferably has the same general size and shape as cover 162, 162*a* to enable it to snap into engagement with base 166, 166*a*. The disposable cover can have a wide variety of internal constructions so long as the IOL is adequately supported (as described above with respect to the other covers) and protected.

Plunger 18 is an elongate member which is adapted to move through the inner passage 115 defined by tubular unit 16 (FIGS. 1 and 13). The plunger comprises a main body 116 preferably shaped with a cross shaped cross section (FIGS. 2–3). As discussed above, one flange 35 of the body is received into groove 34 to ensure proper placement of the plunger. A flat thumb pad 119 is provided on the proximal end of body 116 for manual operation of the device. Other constructions, however, may be provided to effect advancement of plunger 18 through tubular unit 16. The forward end of body 116 includes a pair of spaced apart O-rings 120a, 120b. The O-rings provide a level of resistance to enable a more controlled manual operation of the plunger. The O-rings further help to prevent the plunger from inadvertent movement when the surgeon manipulates device 10 during the surgical procedure. Other constructions, such as friction fit flanges, could be used in place of the O-ring.

Figure 25:
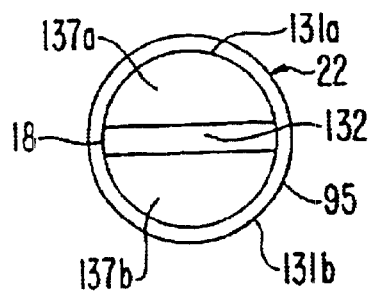
FIG. 25 is a front end view of the insertion device with the plunger extended to the distal end of the cannula.

A slender rod 122 projects forwardly beyond the main body 116 of plunger 18. The rod is intended to pass through staging area 45, funnel 112 and lumen 114. In order to provide sufficient clearance for rod 122, shelf segment 29 defines a channel 124 and cover 21 includes a relief 125 (FIGS. 5–11 and 13–14). Relief 125 only extends partway across cover 21 because surface 88 diverges away from the interior side of shelf segment 29 and thus provides sufficient clearance for rod 122. While rod 122 could have a wide range of shapes, it preferably has a circular or a slight ellipsoid shape adapted to pass through the distal end 95 of cannula 22 (FIG. 25).

The distal tip 128 of rod 122 is preferably bifurcated to define a pair of prongs 131a, 131b separated by a slot 132 (FIGS. 2–3, 16–18, 24 and 25). The slot is shaped to receive and hold proximal haptic 49a and optic 48 of lens 12. The ends 135a, 135b of prongs 131a, 131b are chamfered to form a pair of walls 137a, 137b which collectively form a generally V-shaped configuration. Depending on the sturdiness of the proximal haptic, walls 137a, 137b may or may not engage the proximal end of the optic 48. Prongs 131a, 131b are preferably identical to one another. Nevertheless, one prong 131a can be made narrower than the other prong 131b to allow extra space for the lens 12 to curl and compress during its passage through lumen 114 and into the patient's eye. Under ordinary circumstances, however, the extra space is not needed.

The distal tip of plunger 18 may alternatively be formed with other structural configurations which would hold the lens when the lens is pushed out of the cannula. For example, when implanting an IOL with loop shaped haptics, the plunger may be formed with a closed vertical slot (not shown) along the top of rod 122 in lieu of the open horizontal slot 132. In this arrangement, the lens would be positioned in staging area 45 with the haptics extending from points along the sides of the tubular unit. The haptic, which curls rearwardly would be inserted into the vertical slot when the lens is mounted in the staging area. To avoid inadvertent release of the haptic during shipping and storage, the plunger could be secured in a fixed position through the use of a latch, tape, or other securing means. In any event, the plunger would engage the optic portion of the lens with its distal tip, formed for example with only inclined surfaces like 137a, 137b. When the lens is initially extended beyond cannula 22, the noted haptic would remain entrapped in the slot which would not yet be exposed outside of cannula 22. When release of the lens is desired, the plunger can be pushed slightly farther to expose the vertical slot and free the trapped haptic. The plunger can then be retracted into the tubular unit 16 while the lens remains in the eye.

In one embodiment, a pair of resilient spring elements 140a, 140b extends laterally from rod 122 near the rod's proximal end (FIGS. 2–3). The spring elements function to press against guideways 41 when the free end 128 of rod 122 extends beyond cannula 22. This engagement with guideways 41 forces spring elements 140a, 140b to be pushed backward, and thereby create a biasing force to pull the plunger rearward into tubular unit 16. In the preferred construction, the spring elements (not shown) would extend forwardly, generally parallel with rod 122, from the front end of the main body. In this arrangement, the spring elements would be designed to curl inward upon engagement with guideways 141. Additionally, a coil spring (not shown) may be secured around the plunger/rod to provide the desired biasing force. Of course, other spring arrangements could also be used. The spring may also be omitted and the plunger retracted manually by the surgeon.

Figure 19:
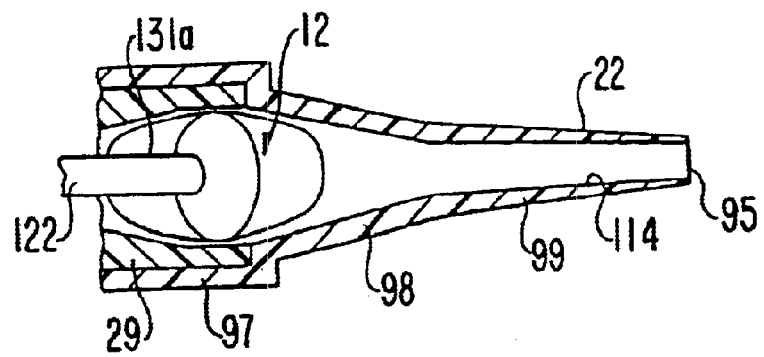
FIGS. 19–23 are each a schematic, partial cross sectional views taken along line 19—19 in FIG. 1, illustrating the movement of the plunger during insertion of the IOL into an eye.
Figure 20:
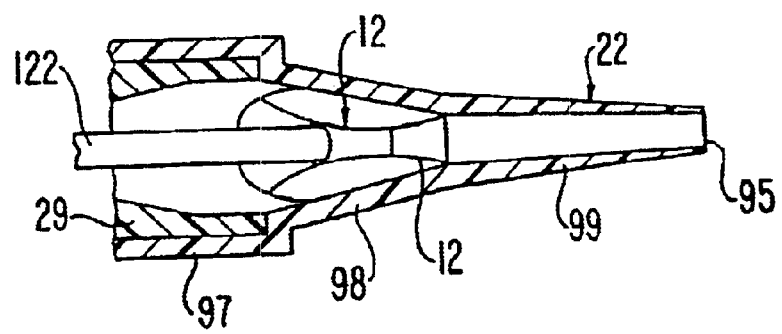
Figure 21:
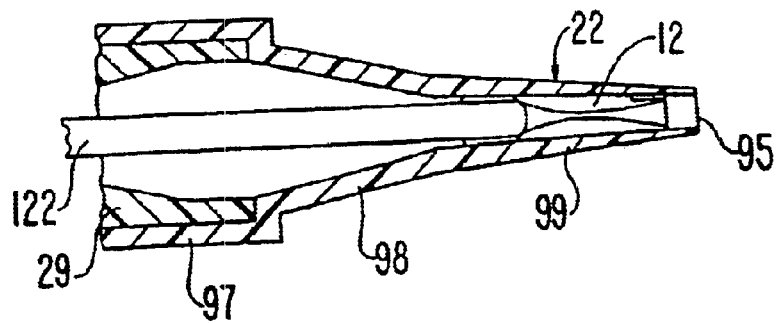

Once the lens has been inspected, device 10 can be assembled. A viscoelastic material, typically used for such surgical procedures, is placed in the cannula 22, typically prior to attachment of the cannula 22 to the assembly, as a lubricant for the insertion process. Once device 10 is assembled, the surgeon inserts the distal end of cannula 22 into the incision 142 in the eye 14. The surgeon then grasps lateral flanges 141 and pushes on pad 119 to move plunger 18 in a continuous forward motion. (FIG. 1). The continuous movement of rod 122 through tubular unit 16 engages lens 12 through its distal end 128 (FIG. 24). the proximal haptic 49a and possibly a portion of optic 48 are received into and held by slot 132, between walls 137a, 137b. The lens is then pushed forwardly by plunger 18 so that the distal side of optic 48 is shifted transversely toward cover 21 by sloped surfaces 59a, 59b of ramps 53a, 53b; that is, sloped surfaces 59a, 59b guide the central portion of optic 48 away from flats 52a, 52b (FIGS. 19 and 20). Inclined surface 88 and conical surface 91 provide ample clearance for this motion of the lens. As the center of the lens is shifted to move over ramps 53a, 53b, the sides of the lens are forced generally in the direction opposite to the ramps, by the inner wall surface 78 of cover 21. Specifically, the conical surface 91 in cover 21 causes lens 12 to curl into troughs 75a, 75b. Continued advancement of lens 12 through the tapering passage of tubular unit 16 causes continued curling and compression of the lens.

The lens continues its forward motion until plunger 18 pushes lens 12 beyond cannula 22. In the preferred construction, plunger 18 is pushed manually forward in a controlled manner, although other means, such as an electric motor or pneumatic drive, may be used.

Figure 22:
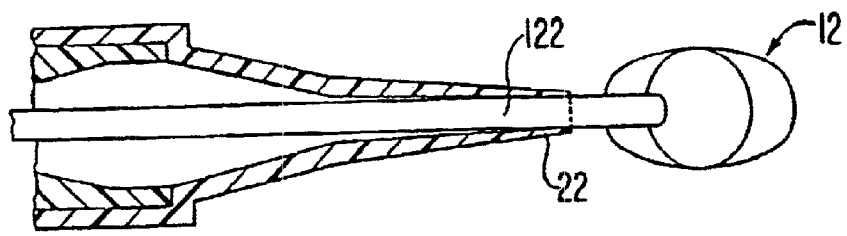
Figure 23:
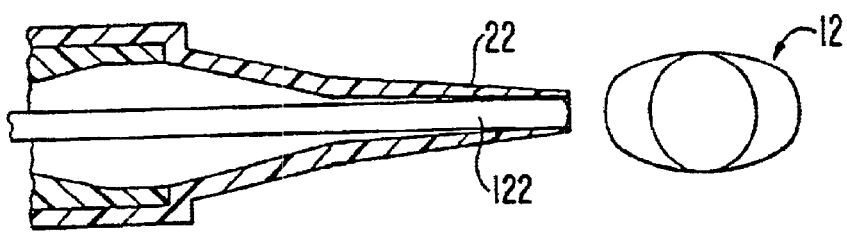

The leading haptic 49b is fed into the distal cul-de-sac 152 of the capsular bag 154. When lens 12 exits from cannula 22, it expands to its full unstressed state (FIGS. 22, 24 and 26). The lens, however, remains held in the slot 132 of plunger 18. Retention of the lens by the plunger reduces the risk of the lens expelling in an uncontrolled manner from the cannula and damaging the interior of the eye. Retaining the lens with the plunger also provides increased control in placing the lens in the eye. To release the lens, the plunger is retracted into tubular unit 16 so that the lens is pushed from slot 132 by distal end 95 of cannula 22 (FIG. 23). The retraction of plunger 18 is preferably performed automatically by biased spring elements 140a, 140b when pressure is released from thumb pad 119. A further implement, or perhaps device 10 itself, will typically be required to properly position the proximal haptic 49a into capsular bag 154.

The above-discussion concerns the preferred embodiments of the present invention. Various other embodiments as well as many changes and alterations may be made without departing from the spirit and broader aspects of the invention as described in the claims. For example, although the preferred embodiments concern the insertion of a flexible IOL into the eye, the invention is not so limited. The teachings of the present invention are applicable to the insertion of flexible membranes generally, including synthetic membranes, biopolymer membranes, and natural body tissues.

What is claimed is:

1. A method of packaging an intraocular lens comprising inserting an intraocular lens having an optic portion into a passage of an inserter adapted to insert the lens into an eye, said intraocular lens being positioned and held by portions of said inserter in a substantially unstressed state with said optic portion suspended to substantially avoid contact thereof with interior portions of said inserter and shipping the inserter with the lens in the passage for distribution to a surgeon for surgical use.

2. A method in accordance with claim 1 in which the intraocular lens is inserted into the passage through an opening defined in a staging area of the inserter, and wherein the method further comprises closing a cover over the opening prior to said shipping of the inserter.

3. A method in accordance with claim 1 wherein said lens further includes a haptic portion, said inserter comprises a tubular member including said passage for receiving said lens, said passage having an open distal end for inserting the lens into an eye and a staging area for supporting the lens in the substantially unstressed state, said staging area including proximal and distal supporting surfaces for supporting the haptic portion of the lens so that the optic portion of the lens is suspended to substantially avoid contact of the optic portion with interior portions of said tubular member in said substantially unstressed state.

4. A method according to claim 3, wherein said inserter further includes a plunger adapted to be movably received within said passage of said tubular member for moving the lens through said open distal end of said tubular member and into the eye.

5. A method in accordance with claim 4 in which said supporting surfaces include at least one distal support which is spaced from sidewalls of said passage to define gaps therebetween, wherein said distal support directs a central portion of the lens in one generally radial direction as said lens is advanced by said plunger to direct folding of said lens in a predetermined direction.

6. A method in accordance with claim 4 in which said plunger includes a distal tip provided with means for holding the lens outside of said passage.

7. A method in accordance with claim 6 which further includes a spring element for retracting said distal tip of said plunger into said passage of said tubular member.

8. A method in accordance with claim 3 in which said passage of said tubular member tapers as it extends from said staging area to said distal end.

9. A method in accordance with claim 3 in which said tubular member includes a cover which can be opened to expose the lens for inspection.

10. A method in accordance with claim 9 in which said tubular member further includes a separate cannula element which is received over said cover to hold said cover in a closed position.

11. A method in accordance with claim 1 and further comprising the step of sterilizing said inserter and said lens together prior to said shipping step.

12. A method in accordance with claim 1, and further comprising the step of providing a cannula for attaching to said inserter immediately prior to said surgical use.

* * * * *

UNITED STATES PATENT AND TRADEMARK OFFICE
CERTIFICATE OF CORRECTION

PATENT NO.     : 6,685,740 B2
DATED          : February 3, 2004
INVENTOR(S)    : Dennis A. Figueroa et al.

It is certified that error appears in the above-identified patent and that said Letters Patent is hereby corrected as shown below:

Column 10,
Line 10, replace "direction as" with -- direction and said gaps receive side portions of the lens in an opposite generally radial direction as --.

Signed and Sealed this

Twenty-fifth Day of May, 2004

JON W. DUDAS
*Acting Director of the United States Patent and Trademark Office*